(12) United States Patent
Hunger et al.

(10) Patent No.: US 10,161,841 B2
(45) Date of Patent: Dec. 25, 2018

(54) CALIBRATION FOR DRILLING RESISTANCE MEASURING DEVICES

(71) Applicant: IML Instrumenta Mechanik Labor System GmbH, Wiesloch (DE)

(72) Inventors: Sebastian Hunger, Wiesloch (DE); Fabian Hunger, Leimen (DE); Erich Hunger, Karlsruhe (DE)

(73) Assignee: IML Instrumenta Mechanik Labor System GmbH, Wiesloch (DE)

( * ) Notice: Subject to any disclaimer, the term of this patent is extended or adjusted under 35 U.S.C. 154(b) by 330 days.

(21) Appl. No.: 14/908,560

(22) PCT Filed: Jul. 29, 2014

(86) PCT No.: PCT/EP2014/002067
§ 371 (c)(1),
(2) Date: Jan. 29, 2016

(87) PCT Pub. No.: WO2015/014482
PCT Pub. Date: Feb. 5, 2015

(65) Prior Publication Data
US 2016/0209308 A1    Jul. 21, 2016

(30) Foreign Application Priority Data
Jul. 29, 2013    (EP) .................................... 13003762

(51) Int. Cl.
*G01N 3/62*    (2006.01)
*G01N 3/58*    (2006.01)
(Continued)

(52) U.S. Cl.
CPC ................. *G01N 3/62* (2013.01); *G01N 3/42* (2013.01); *G01N 3/58* (2013.01); *G01N 33/46* (2013.01)

(58) Field of Classification Search
CPC combination set(s) only.
See application file for complete search history.

(56) References Cited

U.S. PATENT DOCUMENTS 4,649,757 A * 3/1987 Crespin ................. B23Q 17/09
73/1.11
4,917,547 A * 4/1990 Frederickson ....... B23Q 11/006
29/DIG. 88
(Continued)

FOREIGN PATENT DOCUMENTS

DE          92 17 170 U1    5/1993
DE    10 2005 013 752 A1   10/2006
(Continued)

*Primary Examiner* — Robert R Raevis
(74) *Attorney, Agent, or Firm* — Gudrun E. Huckett (57) ABSTRACT

The present invention provides a calibration adapter (1) for drilling resistance measuring devices (10) which have at least one drilling needle receptacle which is coupled to a drive, a drilling needle (15), a guide sleeve (12) with a drilling needle outlet opening and an apparatus for drilling resistance detection and output. The invention further provides a calibration apparatus and a drilling resistance measuring apparatus, and also a method for calibrated drilling resistance measurement. The calibration adapter (1) has a main body (3) which has a coupling apparatus (5) in order to be releasably fastened to the drilling resistance measuring device (10) upstream of the drilling needle outlet opening and a drilling needle passage channel (33) which extends through the main body (3) and which is designed in such a way that it is aligned with the drilling needle outlet opening in a fastening arrangement of the calibration adapter (1) to the drilling resistance measuring device (10). The main body (3) further has at least one receiving space (31) for at least one test body (2). An alignment axis which is provided by the passage channel (33) intersects the at least one receiving space (31).

16 Claims, 6 Drawing Sheets

(51) Int. Cl.
*G01N 33/46* (2006.01)
*G01N 3/42* (2006.01)

(56) References Cited

U.S. PATENT DOCUMENTS

| | | | | |
|---|---|---|---|---|
| 5,231,885 A * | 8/1993 | Suzuki | ............... | G01N 3/58 |
| | | | | 73/862.08 |
| 2005/0013674 A1 * | 1/2005 | Vidal | ............ | B23Q 11/0064 |
| | | | | 408/67 |

FOREIGN PATENT DOCUMENTS

| DE | 10 2009 013 069 A1 | 2/2010 |
|---|---|---|
| EP | 2 028 473 A1 | 2/2009 |

\* cited by examiner

CALIBRATION FOR DRILLING RESISTANCE MEASURING DEVICES

BACKGROUND OF THE INVENTION

The invention concerns a calibration adapter for drilling resistance measuring devices, a calibration apparatus, and a calibratable drilling resistance measuring apparatus as well as a method for calibrated drilling resistance measurement.

Drilling resistance measurements for analysis of materials are known and are used frequently for checking the inner condition of wood objects such as trees, masts, construction lumber etc. but can also be used for other materials such as sandstone or concrete. The drilling resistance that the drilling needle penetrating the object under measurement is experiencing correlates naturally with the density of the object under measurement. Usually, in drilling resistance measurements the drilling needle is pressed with uniform feed into the object under measurement and during the drilling process the energy required therefor is measured as a function of the penetration depth of the needle. The measurement result is represented as a drilling curve, wherein the amplitudes thereof allow conclusions in regard to the drilling resistances and wherein deviations of the properties as well as density differences can be detected based thereon.

In order to obtain meaningful and reproducible measurement results, a calibration of the drilling resistance measuring device is required in order to eliminate other factors that have an influence on the measurement drilling action, for example, the condition of the employed drilling needle.

Manufacturers of drilling resistance measuring devices offer a calibration as a service, for example, in the context of an annual inspection, in order to provide the customer with a high measuring precision and reliability even after extended use of the drilling resistance measuring devices.

DE 92 17 170 U1 discloses for a density measurement by means of drilling resistance measurement a calibration by comparison with a gravimetrically determined density of a drilling core. Non-invasive methods are however preferred because they are less damaging.

EP 20 28 473 A1 discloses a method for examination and evaluation of the stability of wood masts, in particular of telephone poles or power line masts, in which the measurement characteristic lines which corresponds to the actual drilling resistance or a parameter derived therefrom for the strength of the wood or the density of the wood are determined by drilling resistance measurements on the wood mast; reference characteristic lines of the drilling resistance or a parameter derived therefrom of the lower limit for the loadability and damages, damage images, and damage classes are determined based on the comparison of the measurement characteristic lines of the drilling resistance measurements and the reference characteristic lines. In this context, a calibration of the drilling resistance values is carried out by determination of a scaling value based on mast break measurements that corresponds to the slope of a straight line through a cloud of measurement points in a diagram in which measured bending stress values are plotted against calculated bending stress values.

DE 10 2009 013 069 A1 discloses a method for examination of the condition of column-shaped or cylindrical sections of objects in which a drilling resistance measurement is combined with the recording of pressure signals at the circumference of the object section in that the drilling needle is introduced discontinuously so that a pulse tomograph is obtained. Before carrying out the method on an object to be measured, the method can be performed on a calibration body of known material quality in order to obtain comparative measurement values. When the method is then performed on the object to be measured, the obtained pulse tomograph and the obtained drilling resistance measurement can be compared with the corresponding comparative measurement results of the calibration body so that, as a function of the deviations of the obtained values, a damage of the measured object can be determined.

Based on this prior art, it is the object of the present invention to provide an apparatus with which the calibration of a measurement performed with a drilling resistance measuring device can be enabled flexibly in a simple way at many locations.

SUMMARY OF THE INVENTION

This object is solved by a calibration adapter that comprises a main body that comprises a coupling device for releasable fastening of the calibration adapter on the drilling resistance measuring device in front of the drilling needle outlet opening; a drilling needle passage which extends through the main body and is designed such that it is aligned with the drilling needle outlet opening in a fastening arrangement of the calibration adapter on the drilling resistance measuring device; and at least one receiving space for at least one test body, wherein an alignment axis provided by the passage intersects the at least one receiving space.

An appropriate calibration apparatus with which drilling resistance measuring devices can be calibrated is comprised of a calibration adapter as disclosed above and at least one test body having dimensions and a shape that enable an arrangement of the test body in the at least one receiving space of the calibration adapter so that a test section of the test body is positionable completely on the alignment axis defined by the passage.

The object of providing a drilling resistance measuring apparatus with which, without complex evaluations and comparisons, calibrated drilling resistance measurements can be performed in a simple way is solved by the drilling resistance measuring apparatus comprising a drilling resistance measuring device and a calibration apparatus as disclosed above, wherein the calibration adapter of the calibration apparatus is detachably fastened by means of the coupling device of the main body on the drilling resistance measuring device in front of the drilling needle outlet opening.

A calibrated drilling resistance measurement can be performed by a method comprising the steps of  providing a calibration adapter as disclosed above with a test body of a predetermined material with a predetermined material parameter correlated with the drilling resistance,  attaching and fastening the calibration adapter to the drilling resistance measuring device in front of the drilling needle outlet opening so that the passage of the calibration adapter is aligned with the drilling needle outlet opening,  performing a drilling resistance measurement with the drilling resistance measuring device on an object to be measured with uniform feed of the drilling needle, in this context   first penetrating the test body present within the calibration adapter by the drilling needle and recording a drilling resistance calibration signal, further advancing and inserting the drilling needle into the object to be measured and recording a drilling resistance measurement signal, calculating the parameter of the object to be measured based on a difference between the calibration signal and the measurement signal and the predetermined material parameter correlated with the drilling resistance of the test body.

Further developments of the apparatus and the method are disclosed in the respective dependent claims.

A calibration adapter according to the invention is embodied for attachment to a drilling resistance measuring device that usually comprises at least one drilling needle receptacle coupled to a drive and a drilling needle that is guided through an outlet opening in a guide sleeve, as well as a recording and output device of the measured drilling resistance. The drilling resistance is experienced upon penetration into the material to be examined.

The calibration adapter comprises a main body with a coupling device by means of which the calibration adapter is releasably fastened to the drilling resistance measuring device in front of the drilling needle outlet opening. For differently designed drilling resistance measuring devices, corresponding different coupling devices which are matched to the respective drilling resistance measuring device can be provided. A passage for the drilling needle is extending through the main body of the calibration adapter and is designed such that, upon fastening of the calibration adapter to the drilling resistance measuring device, it is aligned with the drilling needle outlet opening. Moreover, the calibration adapter comprises within the main body a receiving space in which a test body can be received at least partially. An alignment axis which is defined by the passage intersects the receiving space so that the test body which is received in the receiving space is positioned with its section (test section) to be examined in front of the passage in order to be drilled through by the drilling needle of the drilling resistance measuring device.

The calibration adapter according to the invention can also comprise two or more receiving spaces for two or more test bodies or a single receiving space can be designed such that two or more test bodies can be received. Since each receiving space is positioned on the alignment axis of the passage, the receiving spaces in the main body are arranged behind each other relative to the alignment axis, wherein the receiving spaces can be separated from each other by walls or can pass into each other.

Of course, the calibration adapter can be used sequentially for several drilling resistance measuring devices or for different types.

Advantageously, with the calibration adapter in a flexible way almost at any time and almost at any location calibrated measuring processes can be performed with the drilling resistance measuring device. Influences on the measurement result such as the condition of the drilling needle can be eliminated by utilization of the calibration adapter. By means of the calibration adapter, a predetermined test body can be placed in a defined position in front of the drilling needle and can be penetrated immediately prior to the actual measurement drilling action wherein more precise and more reproducible results are obtained than without calibration.

Generally, it is conceivable that the main body does not enclose the test body completely so that a side of the test body which is facing away from the passage is exposed. The test body could be secured by gripping engagement or a clamp in front of the passage so that the drilling needle, after penetration of the test body, exits directly and can be introduced into an object to be measured. Preferably however, the test body is engaged in the drilling needle feeding direction at both sides by the main body so that the passage extends through the main body at both sides of the receiving space. In this way, the receiving space can be designed in a simple way as kind of a drawer compartment in the main body into which the test body can be inserted.

So that the test body not only can be inserted and exchanged in a simple way but also secured against accidental removal from the receiving space, the calibration adapter can comprise a removable cover that supplements the main body and that, together with the main body, delimits the receiving space so that the receiving space is opened upon removal of the cover. The through opening which is provided in the cover is aligned accordingly with the passage in the main body provided for the drilling needle so that the through opening and the passage form the entire passageway for the drilling needle in the calibration adapter.

In order to be able to use a test body for several calibration drilling actions, the test body can be supported on one or a plurality of bearing elements so as to be rotatable and/or slidable in the receiving space in a plane perpendicular to the alignment axis that is defined by the passage; in this way, after a complete through drilling action of the test body at a first test section, the test body can be displaced or rotated so that a test section that has not yet been drilled through is positioned aligned with the alignment axis.

In order for the test body that is supported rotatably and/or slidably not to move accidentally during measurement, the calibration adapter can comprise a fixation device with which the test body can be secured in a test position. Alternatively or additionally, the calibration adapter may comprise an actuating device, a detection device, and/or a display device for manual and/or automatic positioning of the test body in the receiving space. An actuating device can comprise, for example, an electrical drive so that the test body is not manually but automatically moved into the new test position after each measurement or after each user input, for example, by pushing a button. An actuating device can also be simply a mechanical component for movement of a test body which is not directly accessible from the exterior of the main body. The detection device can detect a position of the test body and/or the number of drilling actions already performed on the test body. Expediently, such a detection device can be coupled with a display device in order to inform the user when it is time to exchange a test body. A display device can however also be embodied simply by markings on the rim of a test disk that mark circumferential sections for manual transfer of the disk into the next test position.

The coupling device with which the calibration adapter is releasably fastened on the drilling resistance measuring device can comprise locking or clamping devices, including screws, preferably knurled screws, with which the calibration adapter can be fastened by clamping on the drilling needle guide sleeve or a cap surrounding the drilling needle guide sleeve. Alternatively, pins and screws for attachment of the calibration adapter on a front plate of the drilling resistance measuring device are also conceivable as a coupling device. When the drilling resistance measuring device comprises an appropriate counter member, connecting techniques such as a screw or a bayonet closure are also conceivable. When, for example, the drilling needle guide sleeve or the cap has an outer thread, the latter can be brought into engagement with an inner thread which is provided on the main body.

A further subject matter of the invention is a calibration apparatus for drilling resistance measuring devices that, in addition to a calibration adapter according to the invention, comprises at least one test body, also in accordance with the invention, that has dimensions and a shape enabling an arrangement of the test body in the receiving space of the calibration adapter. Accordingly, a test section of the test body is positionable completely on the alignment axis defined by the passage. It has been found that a minimum test body thickness to be drilled through is at least 3 mm, preferably 5 mm, in order to provide a meaningful and reproducible signal. Depending also on the density of the test body, test bodies can also have other thicknesses, e.g. 8 mm or more.

In order to be able to exactly calibrate the drilling resistance measuring device for objects to be measured with different density or strength, the calibration apparatus can comprise two or more test bodies of different materials with known material parameters, such as density or strength etc., correlated with the drilling resistance, wherein one can be arranged in the receiving space, respectively.

When more than one receiving space for test bodies is provided, or the receiving space is configured for receiving a plurality of test bodies, in each receiving space at least one test body can be arranged. For calibration, the test bodies of the various materials can be drilled through; but it is also possible, by an appropriate arrangement of the test bodies in the receiving spaces, to only drill through one test body for calibration, respectively. Positioning of the test bodies in the receiving spaces can be done manually or automatically by an actuating device.

In a preferred embodiment, the test body of the calibration device is configured as a round test disk with a central bore for which, adjacent to the passage, a bearing pin arranged in parallel thereto is provided in the receiving space that is of appropriately round shape so that the test disk is arranged rotatably in the receiving space. With a passage that is preferably extending so as to be centered through the main body, the test disk is thus eccentrically supported in the main body so that the test disk received in the receiving space projects at the same time advantageously partially out of the main body. In this way, the test disk can be rotated comfortably and easily by hand in order to position a test section that has not yet been drilled through in front of the passage. For good gripping action, the rim of the test disk can be profiled.

As an alternative to the test disk, the test body can also be in the form of a strip-shaped test plate, and the receiving space extends perpendicular to the alignment axis straight through the main body so that the test plate can be pushed through the receiving space in order to position the test section in front of the passage, respectively.

In calibration adapters with a plurality of receiving spaces, it is also possible to combine both test body variants.

A drilling resistance measuring apparatus according to the invention comprises a drilling resistance measuring device that comprises at least one drilling needle receptacle coupled to a drive, a drilling needle, a guide sleeve with a drilling needle outlet opening, and a drilling resistance recording and output. Moreover, this drilling resistance measuring apparatus comprises the calibration apparatus according to the invention which, in turn, is comprised of the calibration adapter according to the invention and a suitable test body as described above. The calibration adapter is detachably fastened by means of the coupling device of the main body to the drilling resistance measuring device in front of the drilling needle outlet opening. With this drilling resistance measuring apparatus it is possible in a simple and effortless way to perform calibrated drilling resistance measurements.

For performing a method according to the invention for calibrated drilling resistance measurement, first a calibration adapter according to the invention is provided and a test body of a predetermined material with a predetermined material parameter correlated with the drilling resistance, for example, density, strength etc., is placed into its receiving space. The calibration adapter is placed onto the drilling resistance measuring device and fastened thereto, wherein the passage of the calibration adapter is aligned with the drilling needle outlet opening in the drilling needle guide sleeve. For performing the drilling resistance measurement with the drilling resistance measuring device on an object to be measured, the drilling needle is driven at uniform feed so that it penetrates first the test body present within the calibration adapter, wherein the drilling resistance measuring device records a drilling resistance calibration signal. Subsequently, the drilling needle is advanced farther and introduced into the object to be measured, wherein a drilling resistance measurement signal is recorded. Based on the difference between the calibration signal and the measurement signal and the predetermined material parameter of the test body correlated with the drilling resistance, the corresponding parameter of the measured object can be calculated.

When the drilling resistance measuring device is calibrated in this way, after retraction of the drilling needle further drilling resistance measurements at the same object to be measured can be performed without calibration. For performing a further calibrated drilling resistance measurement, after retraction of the drilling needle the position of the test body in the receiving space in a plane perpendicular to the alignment axis is changed so that a test section of the test body which has not yet been drilled through is positioned in front of the passage. Alternatively or when all test sections have been drilled through, the test body can be exchanged.

When providing the calibration adapter for performing a calibrated measurement, preferably a test body with a material parameter can be selected whose magnitude is within the range of magnitude of a material parameter expected of the object to be measured so that an even more precise result will be obtained.

BRIEF DESCRIPTION OF THE DRAWINGS

These and further advantages will be explained in the following description with reference to the attached figures. The reference to the figures in the description serves for aiding the description and for facilitating understanding of the subject matter. Elements or parts of the elements which are substantially identical or similar may be identified with the same reference characters. The figures are only a schematic illustration of an embodiment of the invention. It is shown in.

DESCRIPTION OF PREFERRED EMBODIMENTS

The invention concerns a calibration adapter which can be placed onto a drilling resistance measuring device for performing calibrated drilling resistance measurements.

Figure 1:
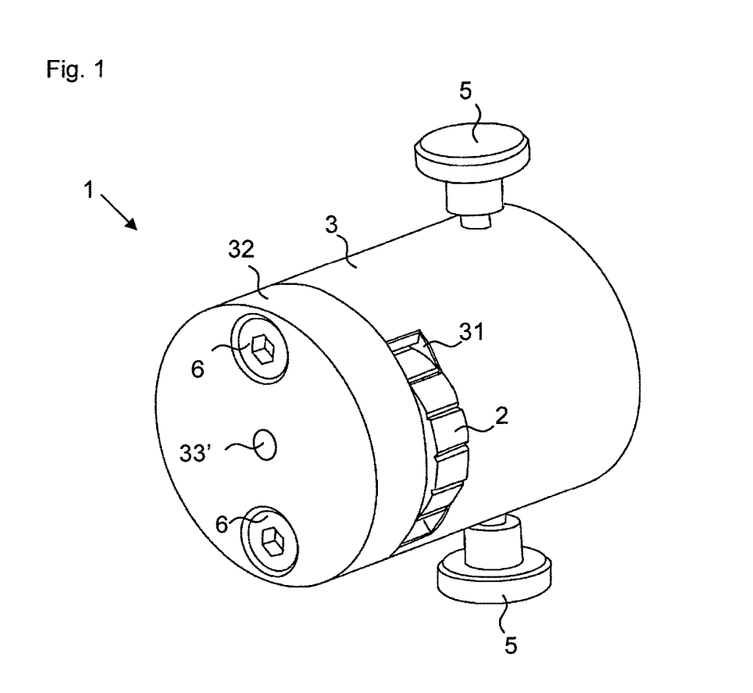
FIG. 1 a perspective view of an embodiment of the calibration apparatus according to the invention of calibration adapter and test disk.
Figure 2:
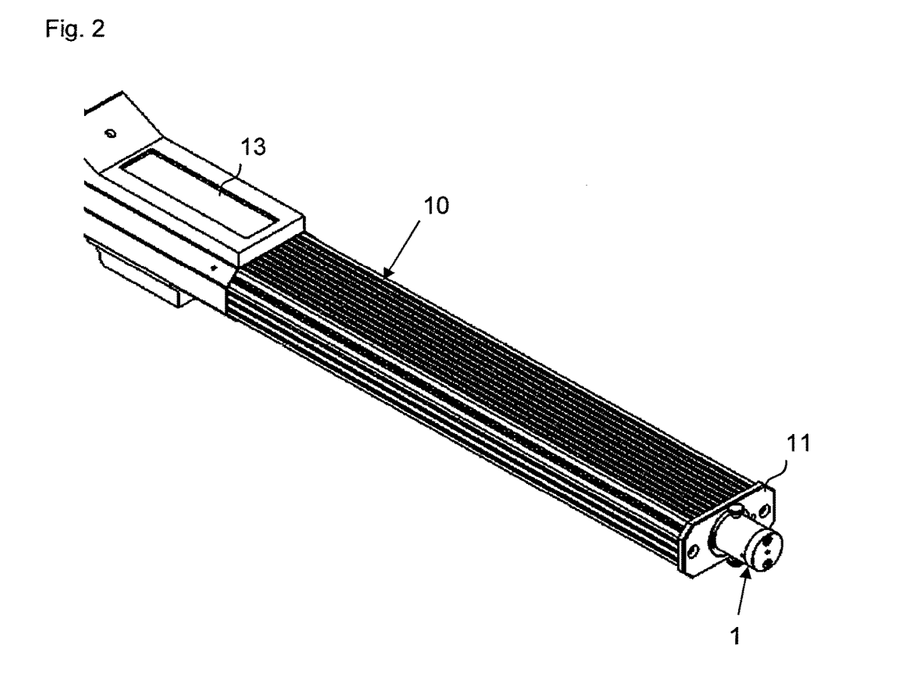
FIG. 2 a perspective view of a drilling resistance measuring device provided with a calibration adapter.

FIG. 1 shows a calibration adapter 1 according to the invention which can be plugged onto a drilling resistance measuring device 10, as can be seen in FIG. 2, and which in the present example is secured with two knurled screws 5. Usually, in the front plate 11 of a drilling resistance measuring device 10 a drilling needle guide sleeve 12 is provided which, in the present case, is also surrounded by a cap 14 (compare FIG. 5 and FIG. 6). The calibration adapter 1, i.e., its main body 3, is designed in this context such that it can be placed with precise fit onto the cap 14 and contacts the front plate 11. In the present case, this means that the main body 3 comprises a cylindrical recess matched to the cap 14. For other drilling resistance measuring devices that are not provided with such a cap or provided with another type of drilling needle guide, alternative main body shapes or different fitting pieces can be provided with which the calibration adapter can be adjusted to the corresponding drilling resistance measuring device.

Fastening of the plugged-in calibration adapter 1, as shown in FIGS. 1 to 4 and 6, can be realized by knurled screws 5 which, by being tightened, clamp the calibration adapter 1 on the cap 14.

The precise fit of the calibration adapter 1 enables the drilling needle which is exiting from the drilling needle guide 12 to precisely enter the passage 33 of the calibration adapter 1 which is extending to the receiving space 31 with the test body 2 positioned between the main body 3 and the cover 32. The test body 2 is a round test disk 2 in the illustrated embodiment. When performing a drilling resistance measurement, this test disk 2 is penetrated by the advancing drilling needle before the drilling needle exits from the outlet opening 33' of the cover 32 and penetrates into the object to be measured. The measurement signals which are obtained upon penetration of the test disk 2 serve for calibration of the directly subsequently performed measurement on the object to be measured.

The test disk 2 is supported eccentrically and rotatably relative to the passage 33 so that by simple rotation of the test disk 2 several test drilling actions can be performed on a test disk 2. In order to facilitate rotation, the test disk 2 has a profiled rim. For simple exchange of the test disk 2, the cover 32 is attached with two screws 6 on the main body 3.

In the calibration adapter according to the invention, different test disks can be arranged which are different with regard to their material and thus with regard to their density or strength. This is important inasmuch as the calibration for the subsequent measurement is all the more precise when the strength of the test disk is similar to the expected strength of the object to be measured. For example, test disks with high strength, for example, made of carbon (carbon fiber-reinforced plastic material) with 13 MPa, can be used for calibration of a measurement on hardwood (for example, maple or oak) while test disks of plastic material, for example, Teflon, exhibit reduced strengths and can be provided for calibration of a measurement on correspondingly softer wood (e.g. coniferous wood).

Further conceivable materials for test bodies are any materials of a homogenous material whose properties are known and that are suitable for measurement on different materials such as wood or stone, i.e., materials with possibly inhomogeneous density that are to be examined. The test body exhibits expediently a homogenous density and strength so that a clear, reproducible calibration signal is obtained.

Figure 3:
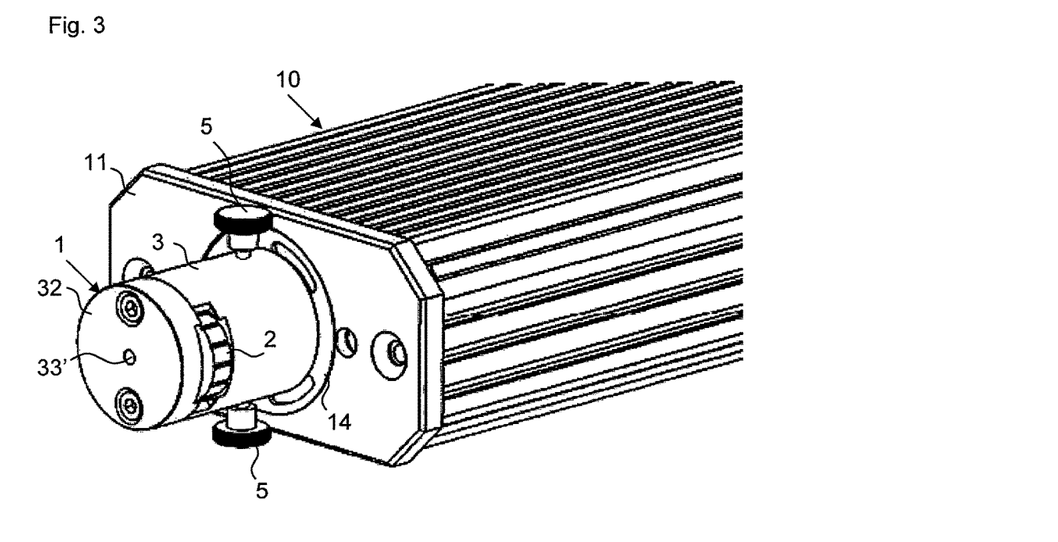
FIG. 3 a detail view of the calibration adapter which is placed onto the drilling resistance measuring device.
Figure 4:
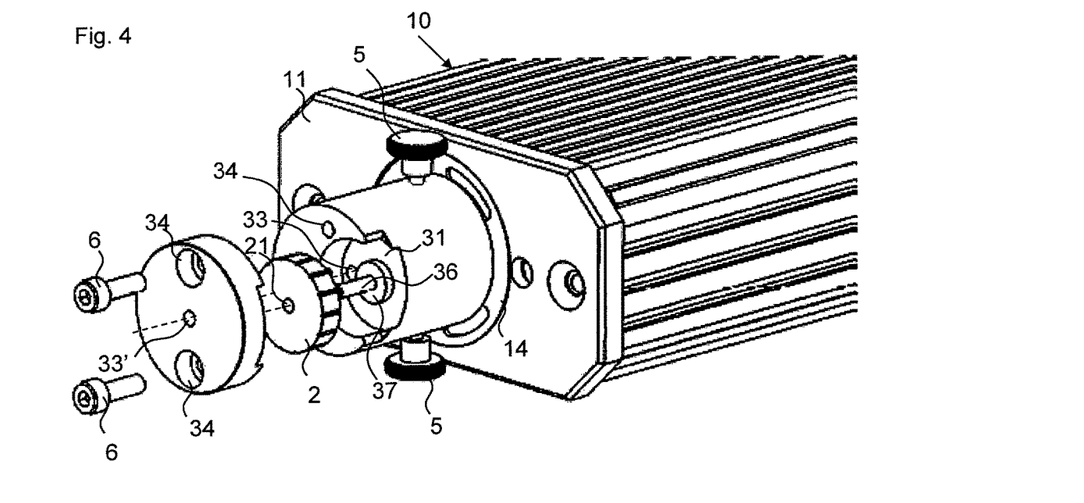
FIG. 4 a partially exploded view of the calibration adapter of FIG. 3 placed onto the drilling resistance measuring device.

FIG. 3 shows the calibration adapter 1 which is placed onto the drilling resistance measuring device 10 and is shown in FIG. 4 in a partially exploded view in which the cover 32 and the test disk 2 are lifted off the main body 3. For a precise fit arrangement of the cover 32 on the main body 3 so that the passage 33 and the through opening 33' for the drilling needle are exactly aligned, there are also aligned bores 34 provided in the main body 3 and in the cover 32 for receiving the screws 6. In the exploded illustration, the bearing pin 36 displaced relative to the passage 33 can be seen on which the test disk 2 is arranged with its central bore 21. A step 37 which is positioned within the main body 3 and in the cover 32 (see FIG. 5) ensures axial fixation of the test disk 2 in the receiving space 31.

In the section views from below (FIG. 5) and from the side (FIG. 6), the precise fit of the main body 3 on the cap 14 of the drilling resistance measuring device 10 can be seen in addition to the bearing action of the test disk 2 in the receiving space 31 between main body 3 and cover 32. In the outer circumference of the section of the cap 14 that surrounds the drilling needle guide sleeve 12, a groove 14' is introduced which is engaged by the knurled screws 5, as can be seen in FIG. 6.

Figure 5:
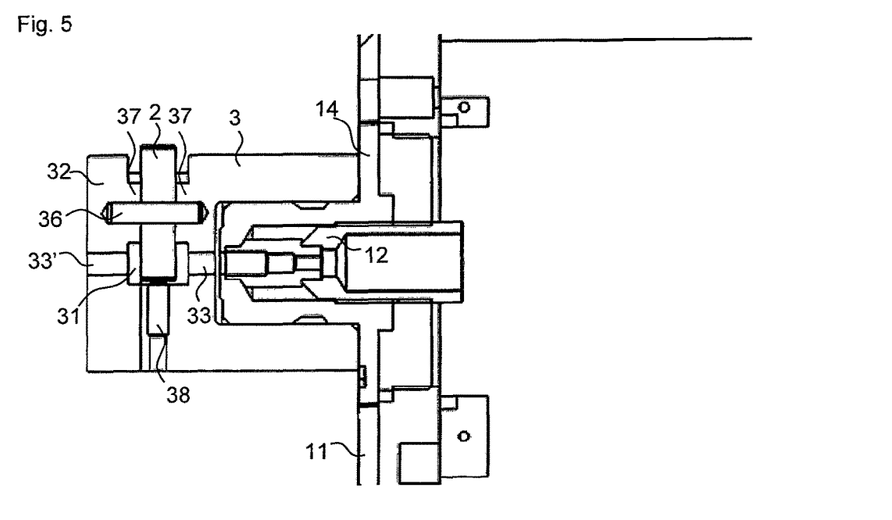
FIG. 5 a section view from below through the calibration adapter of FIG. 3 placed onto the drilling resistance measuring device.
Figure 6:
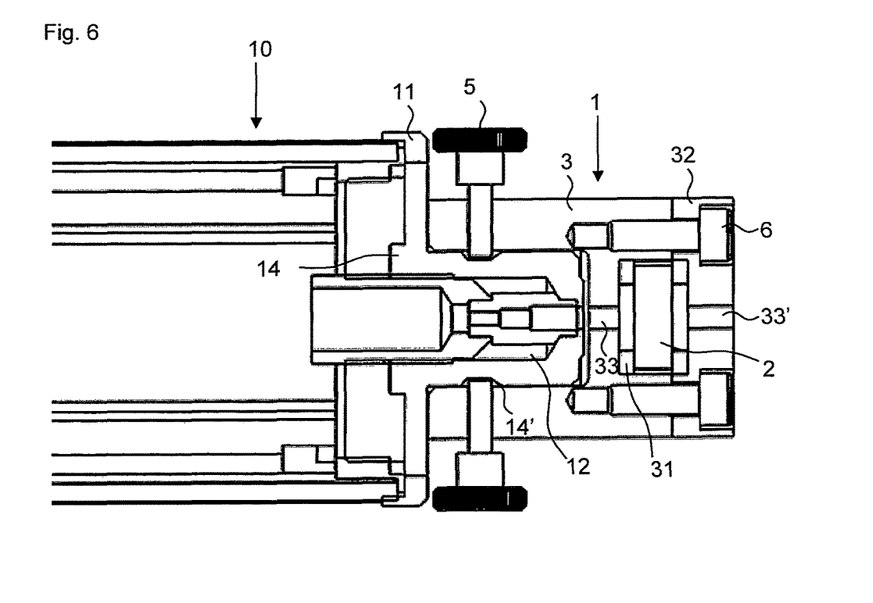
FIG. 6 a lateral section view of the calibration adapter of FIG. 3 placed onto the drilling resistance measuring device.

In FIG. 5, a fixation device comprising a securing pin 38 is also shown that is provided in the main body 3 and whose head projects into the receiving opening 31 and is engaging the test disk 2 in order to secure the test disk 2 during the measuring process so that it is not accidentally rotated. Advantageously, for this purpose notches of the profiled rim of the test disk 2 can be utilized as engaging positions. The fixation device comprising the securing pin 38 can be provided with a pretension for these engagement positions, for example, by means of a spring. This pretension is sufficient for fixation of the test disk 2 during the measuring process but can be easily overcome upon rotation of the test disk 2 so that the securing pin 38 can be pushed out of the notch in the rim of the test disk 2. The head of the securing pin 38 can thus form a locking nose which is in particular advantageous when the circumferential spacings between the notches are selected such that the test disk 2, when it is to be transferred by rotation into the next test position after completed measurement, automatically assumes, upon locking in the next notch, the next test position in which a section not yet drilled through is positioned in front of the passage 33.

It is not mandatorily required that a calibration is carried out prior to each measurement. For example, the test disk can also be left in its position when, for example, a plurality of measurements are to be realized on one object to be measured or when several identical objects to be measured are to be examined. After completed calibration, the drilling needle then passes in the subsequent measurements through the drilled-through location in the test disk without new calibration.

Alternatively or additionally to notches at proper spacing, other markings can be provided also on the test disk 2 or its rim which indicate to the user how far the test disk 2 must be moved in order to reach the next test position. Moreover, in particular in connection with a locking securing pin 38, a counter or a similar device can be integrated so that it is indicated to the user when all test positions of the test disk 2 have been utilized and the test disk 2 must be exchanged.

FIGS. 1 to 6 show the test body in an exemplary fashion as a round disk which can be simply rotated advantageously for performing further calibrated measurements. However, other geometries for a test body are also conceivable, for example, rectangular strip-like shapes that, for example, can then be pushed through the receiving space, instead of being rotated, in order to assume further test positions.

Figure 7:
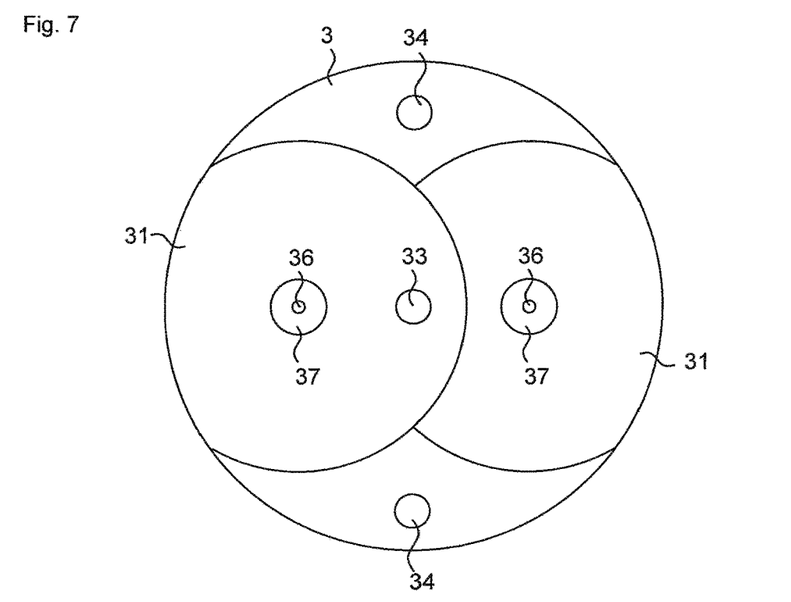
FIG. 7 a front view of a calibration adapter without cover with two receiving spaces that are adjoining each other and are of the same configuration.
Figure 8:
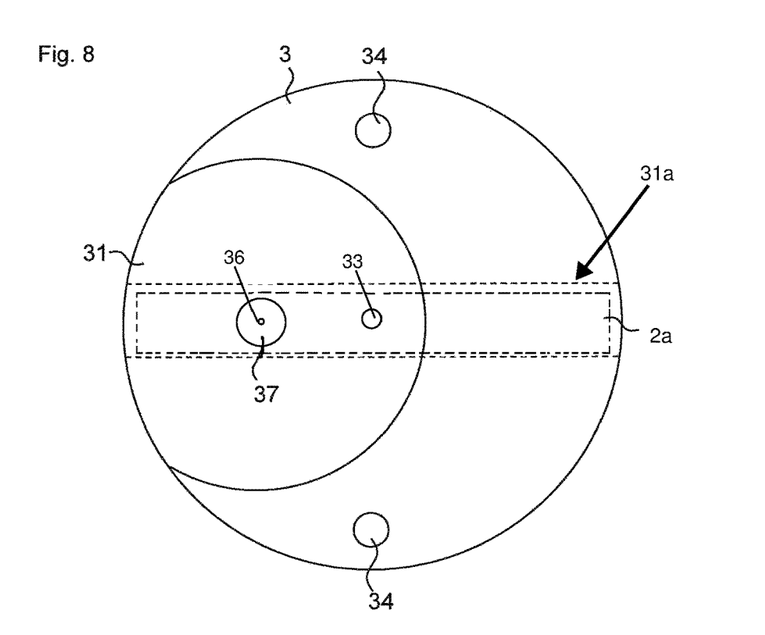
FIG. 8 a front view of a calibration adapter without cover with two receiving spaces that are axially spaced from each other and are configured differently.

FIG. 7 and FIG. 8 show in an exemplary fashion two possible variants of a calibration adapter according to the invention having in its main body 3 two receiving spaces 31. In FIG. 7, the two receiving spaces 31 are displaced axially behind each other; the alignment axis defined by the passage 33 intersects thus both receiving spaces 31. The receiving space 31 which is positioned in the plane of the drawing father to the rear and to the left has, like the forwardly positioned one, a step 37 for axial fixation of a test disk (not illustrated in FIG. 7) received on the bearing pin 36. The counter bearing which is provided in the cover and is not shown is designed correspondingly, i.e., the step for axial fixation, which is correlated with the left "remote" receiving space 31, projects father away from the cover than the right "closer" receiving space 31.

FIG. 8 shows schematically a calibration adapter according to the invention which has a round receiving space 31 as described above that is delimited by the cover (not illustrated) and that comprises a compartment as a second receiving space 31a that extends linearly through the main body 3 and is positioned in the plane of the drawing father to the rear and therefore is illustrated in dashed lines. In this compartment, a corresponding strip-shaped test plate 2a (shown in dashed lines) can be arranged and pushed through to assume further test positions.

It is not mandatorily required that several test bodies are arranged in the calibration adapters with more than one receiving space; it is also possible to utilize only one of the receiving spaces. When performing the calibrated drilling resistance measurements, several test disks with different densities can be drilled through, as needed, and several calibration signals can be obtained in this way; but it is also possible that only one test disk whose density is approximately corresponding to the expected density of the object to be measured is positioned with a not yet drilled-through section in test position in front of the passage. The other test body or the other test bodies can be arranged outside of the alignment axis or can be positioned with an already drilled-through test section on the alignment axis so that the drilling needle does not drill through this test body again.

Figure 9:
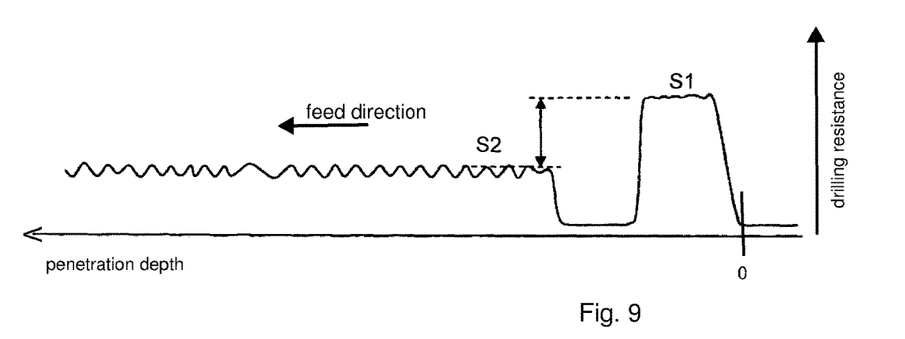
FIG. 9 a first drilling curve obtained with the drilling resistance measuring device according to the invention.
Figure 10:
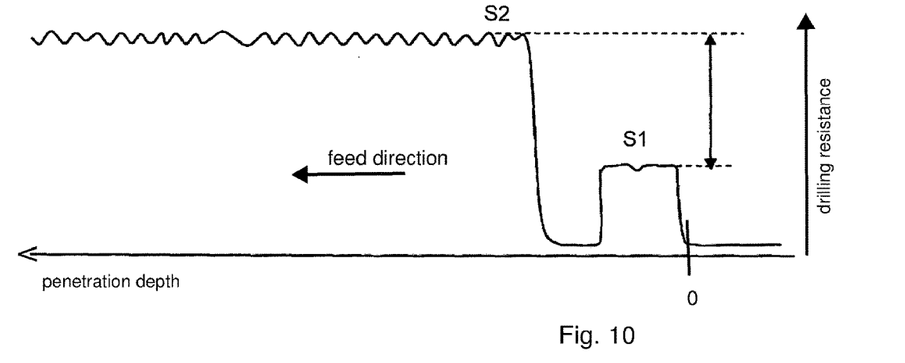
FIG. 10 a second drilling curve obtained with the drilling resistance measuring device according to the invention.
Figure 11:
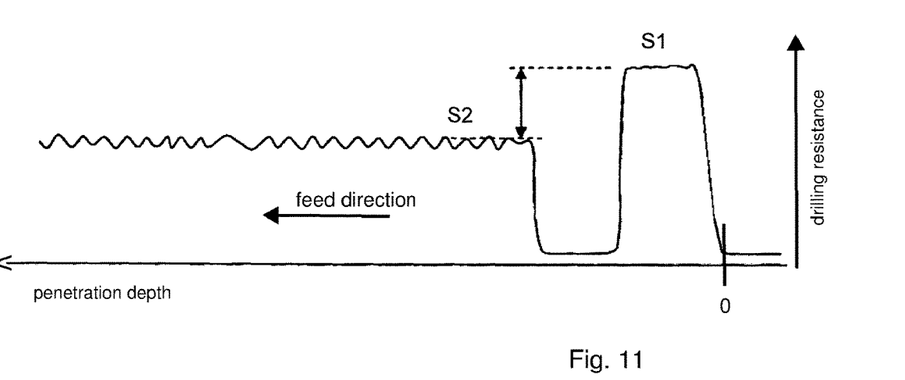
FIG. 11 a third drilling curve obtained with the drilling resistance measuring device according to the invention.
Figure 12:
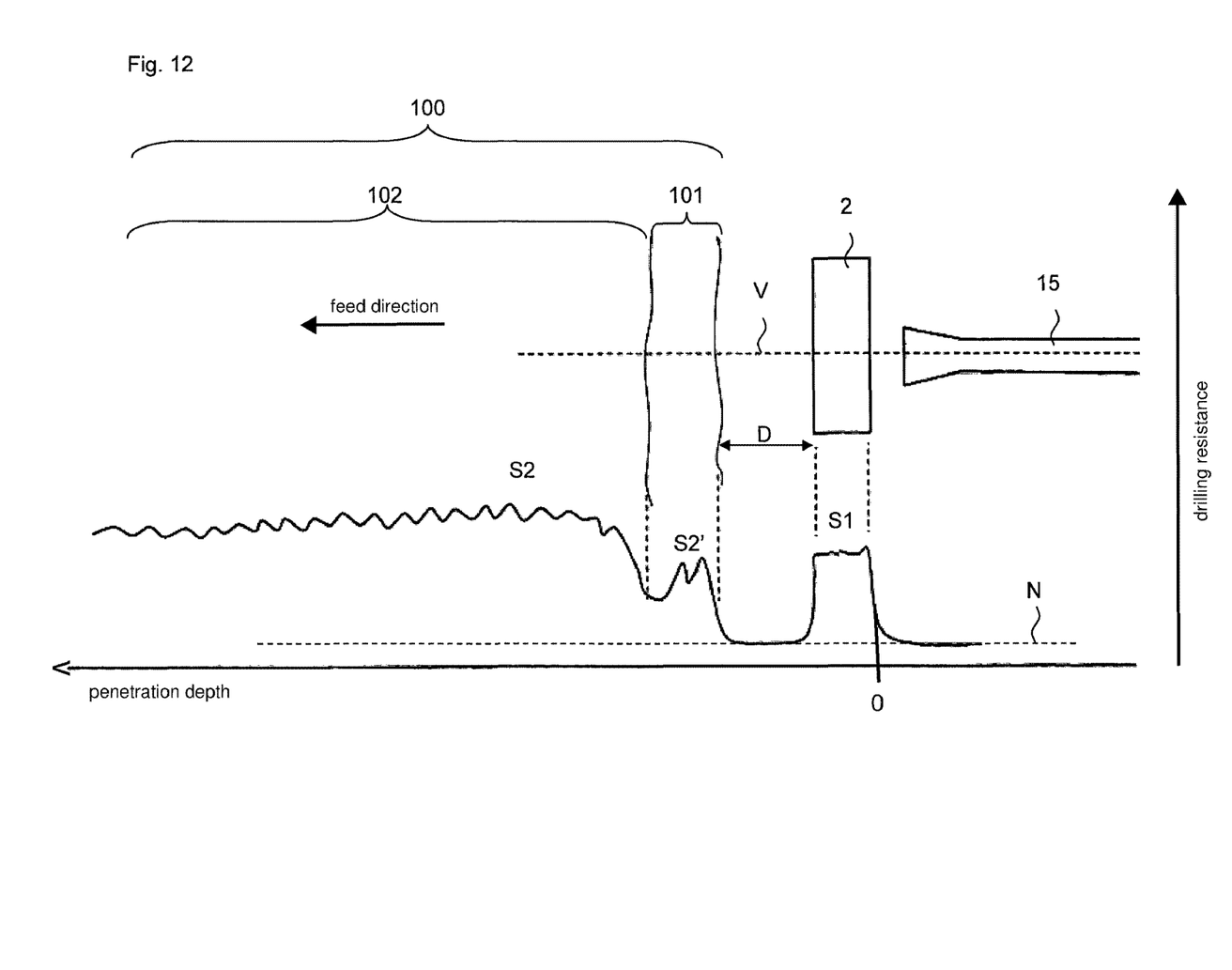
FIG. 12 a further drilling curve correlated in schematic illustration with the test body and the object under measurement.

FIGS. 9 through 11 show drilling curves as they are obtained by calibrated drilling resistance measurements performed according to the invention. FIG. 12 illustrates how the measured signals S1 and S2 of a drilling curve are obtained. For performing a calibrated drilling resistant measurement, the drilling needle 15 is advanced and penetrates first the test body 2 which has been positioned by means of the calibration adapter (not illustrated here) in the feed direction V (=alignment axis of the passage) so that the calibration signal S1 is recorded before the drilling needle 15 penetrates into the object to be measured 100, for example, a tree, whereby the measuring signal S2 is obtained. The measuring signal S2' is generated upon penetration of the tree bark 101 comprised of bark and bast whose density deviates from the density of the wood 102 in the interior of the tree 100. Between test body 2 and the object to be measured 100 the drilling needle 15 must travel a certain distance D which is predetermined by the cover of the calibration adapter in which the drilling needle 15 passes through the through opening in the cover and is experiencing no drilling resistance; this can be seen in the drilling curve by the drop to the zero line N.

In general, for performing a calibrated drilling resistance measurement according to the invention, first a calibration adapter according to the invention with a test body of predetermined density or strength is provided and is attached and fastened to the drilling resistance measuring device so that the passage of the calibration adapter is aligned with the drilling needle guide in the drilling needle guide sleeve. The drilling resistance measuring device is placed against the object to be measured and the drilling resistance measurement is started by advancing the drilling needle. First, the drilling needle penetrates the test body which is arranged in the calibration adapter and records in this context based on the drilling resistance the calibration signal S1 which correlates with the density or strength of the test body. Without removing the drilling resistance measuring device, the measurement is continued and the drilling needle is farther advanced so that, after passing through the calibration adapter, it penetrates into the object to be measured and thereby, by means of the drilling resistance, records the measuring signal S2 correlated with the density or strength of the object to be measured. Based on the difference between the drilling resistance calibration signal, the drilling resistance measurement signal, and the predetermined density or strength of the test body, the density or strength of the measured object can be calculated.

Output parameters of the drilling resistance measuring device can be the drilling resistance measurement signal S2, the calibration signal S1, or the difference of the two signals so that the user can perform in a simple way the calculation of the desired parameter, be it the density of the measured object or another parameter that can be correlated with the drilling resistance, in knowledge of the corresponding size of the test body.

FIG. 9 shows the drilling curve of a calibrated measurement in which the measurement signal S2 is smaller than the calibration signal S1 which indicates that the wood has a smaller density than the test body. For evaluation of the drilling curve the difference between the measurement signals S1 and S2 is used as a measurement value so that artificial effects on the measurement as they can be caused by use of a blunt drilling needle are eliminated. This is apparent in particular when comparing the drilling curve of FIG. 9 (drilling needle is proper) with the drilling curve of FIG. 11 (blunt drilling needle) which provide the same difference S1-S2 even though the absolute drilling resistances differ significantly. With the preceding calibration by means of the test body, the same result is obtained independent of the quality of the employed drilling needle.

FIG. 10 shows an example of a drilling curve with the calibration signal S1 and the measurement signal S2 from which it can be derived that the wooden measured object has a density that is greater than that of the test material.

Many drilling resistance measuring devices with integrated computer unit provide already evaluated measurement curves; by means of menu selections that are, for example, displayed on a display 13 of the drilling resistance measuring device 10 (compare FIG. 2), it can be selected whether the measurement value is to be output as drilling resistance or density or optionally also another material parameter.

The calibrated measurement can be advantageously also automatically processed when in the computer of the drilling resistance measuring device a corresponding input is made in regard to the material parameter of interest, for example, density or strength etc. of the test body. In this case, the desired parameter can be output precisely and directly. Further calculations are not required.

In case of a drilling resistance measuring device with integrated computer, it is moreover conceivable that one can select from a menu and display on a display whether a measurement to be performed is performed with or without calibration with the corresponding correlated evaluation.

What is claimed is:

1. A calibration adapter for a drilling resistance measuring device, the drilling resistance measuring device comprising at least one drilling needle receptacle coupled to a drive, a drilling needle, a guide sleeve comprising a drilling needle outlet opening, and a device for drilling resistance recording and output, wherein the calibration adapter comprises:
    a main body that comprises:
        a coupling device configured to releasably fasten the calibration adapter on the drilling resistance measuring device in front of the drilling needle outlet opening;
        a drilling needle passage extending through the main body and aligned with the drilling needle outlet opening when the calibration adapter is fastened on the drilling resistance measuring device;
        at least one receiving space configured to receive at least one test body, wherein an alignment axis defined by the drilling needle passage intersects the at least one receiving space;
        wherein the at least one receiving space is selected from the group consisting of:
            a linear compartment extending orthogonally to the alignment axis through the main body and configured to enable slidability of the at least one test body in a plane orthogonal to the alignment axis;
            a round receiving space in which a bearing pin is arranged parallel to the alignment axis and spaced apart from the alignment axis, wherein the bearing pin is configured to rotatably support the at least one test body for rotation in a plane orthogonal to the alignment axis; and
            a combination of said linear compartment and of said round receiving space.

2. The calibration adapter according to claim 1, further comprising a cover connected removably to the main body, wherein the cover and the main body together delimit the at least one receiving space, wherein the cover comprises a through opening that is aligned with the drilling needle passage.

3. The calibration adapter according to claim 1, further comprising a fixation device configured to secure the at least one test body.

4. The calibration adapter according to claim 1, wherein the coupling device comprises one or more clamping devices configured to fasten by clamping the calibration adapter on the drilling needle guide sleeve or on a cap surrounding the drilling needle guide sleeve.

5. The calibration adapter according to claim 4, wherein the clamping devices are screws or knurled screws.

6. A calibration apparatus for a drilling resistance measuring device, the drilling resistance measuring device comprising at least one drilling needle receptacle coupled to a drive, a drilling needle, a guide sleeve comprising a drilling needle outlet opening, and a device for drilling resistance recording and output, wherein the calibration apparatus comprises:
    at least one test body;
    a calibration adapter comprising a main body that comprises:
        a coupling device configured to releasably fasten the calibration adapter on the drilling resistance measuring device in front of the drilling needle outlet opening;
        a drilling needle passage extending through the main body and aligned with the drilling needle outlet opening when the calibration adapter is fastened on the drilling resistance measuring device;
        at least one receiving space configured to receive the at least one test body, wherein an alignment axis defined by the drilling needle passage intersects the at least one receiving space;
        wherein the at least one receiving space is selected from the group consisting of:
            a linear compartment extending orthogonally to the alignment axis through the main body and configured to enable slidability of the at least one test body in a plane orthogonal to the alignment axis;
            a round receiving space in which a bearing pin is arranged parallel to the alignment axis and spaced apart from the alignment axis, wherein the bearing pin is configured to rotatably support the at least one test body for rotation in a plane orthogonal to the alignment axis; and
            a combination of said linear compartment and of said round receiving space;
    wherein the at least one test body has dimensions and a shape enabling an arrangement of the at least one test body in the at least one receiving space of the calibration adapter so that a test section of the at least one test body is positionable completely on the alignment axis defined by the drilling needle passage.

7. The calibration apparatus according to claim 6, wherein two of said at least one test body are provided that are comprised of different materials, respectively, wherein the different materials have known material parameters correlated with a drilling resistance of the different materials, respectively, wherein one of said two test bodies is arranged in one of the receiving spaces, respectively.

8. The calibration apparatus according to claim 7, wherein the at least one test body is a test disk with a central bore and the central bore is configured to be rotatably arranged on the bearing pin of the round receiving space.

9. The calibration apparatus according to claim 8, wherein the test disk, when received in the at least one receiving space, projects partially away from the main body of the calibration adapter and comprises a profiled rim.

10. The calibration apparatus according to claim 6, wherein the at least one test body is a strip-like test plate, wherein the test plate is pushed through the at least one receiving space that is in the form of the linear compartment, extending orthogonally to the alignment axis through the main body, in a direction orthogonal to the alignment axis.

11. A drilling resistance measuring apparatus comprising a drilling resistance measuring device and a calibration apparatus according to claim 6, wherein the calibration adapter of the calibration apparatus is detachably fastened by the coupling device of the main body of the calibration adapter on the drilling resistance measuring device in front of a drilling needle outlet opening of the drilling resistance measuring device.

12. A method for calibrated drilling resistance measurement, the method comprising the steps of:
- providing a calibration adapter comprising a main body that comprises a coupling device configured to releasably fasten the calibration adapter on a drilling resistance measuring device in front of a drilling needle outlet opening: a drilling needle passage extending through the main body and aligned with the drilling needle outlet opening when the calibration adapter is fastened on the drilling resistance measuring device; and at least one receiving space configured to receive at least one test body, wherein an alignment axis defined by the drilling needle passage intersects the at least one receiving space;
- arranging in the calibration adapter a test body of a predetermined material with a predetermined material parameter correlated with the drilling resistance of the test body;
- attaching and fastening the calibration adapter to the drilling resistance measuring device in front of a drilling needle outlet opening of the drilling resistance measuring device so that the drilling needle passage of the calibration adapter is aligned with the drilling needle outlet opening;
- performing a drilling resistance measurement with the drilling resistance measuring device on an object to be measured with uniform feed of the drilling needle by:
  - first penetrating the test body in the calibration adapter by a drilling needle of the drilling resistance measuring device and recording a drilling resistance calibration signal,
  - further advancing and inserting the drilling needle into the object to be measured and recording a first drilling resistance measurement signal,
  - calculating a material parameter of the object to be measured based on a difference between the drilling resistance calibration signal and the first drilling resistance measurement signal and based on the predetermined material parameter correlated with the drilling resistance of the test body.

13. The method according to claim 12, further comprising the steps of:
- retracting the drilling needle;
- performing a second drilling resistance measurement with the test body remaining in its position in the calibration adapter and using the drilling resistance calibration signal for the second drilling resistance measurement.

14. The method according to claim 12, further comprising the steps of:
- retracting the drilling needle;
- changing the position of the test body by rotating and/or sliding the test body in the receiving space of the calibration adapter in a plane orthogonal to the alignment axis of the drilling needle passage of the calibration adapter so that a test section that has not yet been drilled through of the test body is positioned on the alignment axis;
- performing a second calibrated drilling resistance measurement.

15. The method according to claim 12, further comprising the steps of:
- retracting the drilling needle;
- exchanging the test body.

16. The method according to claim 12, further comprising the step of selecting the test body to have a material parameter whose magnitude is in a range of magnitude of an expected material parameter of the object to be measured.

* * * * *